United States Patent [19]

Bentley et al.

[11] Patent Number: 5,347,008
[45] Date of Patent: Sep. 13, 1994

[54] THIO(CYCLO) ALKANEPOLYCARBOXYLIC ACIDS CONTAINING HETEROCYCLIC SUBSTITUENTS

[75] Inventors: Robert L. Bentley, Urmston; Michael P. Savage, Heald Green; Kenneth W. Shelton, Brooklands, all of United Kingdom

[73] Assignee: Ciba-Geigy Corporation, Ardsley, N.Y.

[21] Appl. No.: 975,153

[22] Filed: Nov. 12, 1992

Related U.S. Application Data

[63] Continuation of Ser. No. 348,096, May 3, 1989, abandoned, which is a continuation of Ser. No. 865,946, May 19, 1986, abandoned, which is a continuation of Ser. No. 610,146, May 14, 1984, abandoned.

[30] Foreign Application Priority Data

May 14, 1983 [GB] United Kingdom ............... 8313322

[51] Int. Cl.$^5$ ........................................ C07D 277/74
[52] U.S. Cl. .................................................. 548/170
[58] Field of Search .......................................... 548/170

[56] References Cited

U.S. PATENT DOCUMENTS

| | | | |
|---|---|---|---|
| 2,535,876 | 12/1950 | Stewart | 548/170 |
| 2,725,364 | 11/1955 | Dazzi | 548/170 |
| 2,725,382 | 11/1955 | Harman | 548/170 |
| 2,939,789 | 6/1960 | Dersch et al. | 548/170 |
| 4,052,160 | 10/1977 | Cook et al. | 21/2.7 A |
| 4,208,344 | 6/1980 | Dingwall et al. | 260/502.4 A |
| 4,294,839 | 10/1981 | Doll | 548/170 |
| 4,329,381 | 5/1982 | Eschway et al. | 427/386 |
| 4,366,076 | 12/1982 | Clark | 252/34 |
| 4,402,907 | 9/1983 | Clark | 544/196 |
| 4,568,753 | 2/1986 | Akashi et al. | 548/174 |
| 4,652,653 | 3/1987 | Baumann et al. | 548/170 |
| 4,746,351 | 5/1988 | Nielsen | 548/170 |

FOREIGN PATENT DOCUMENTS

| | | | |
|---|---|---|---|
| 93908 | 11/1983 | European Pat. Off. | |
| 3064 | 1/1979 | Japan | 548/170 |
| 54-3064 | 1/1979 | Japan | |
| 118554 | 7/1982 | Japan | 548/170 |
| 204183 | 11/1983 | Japan | 548/170 |
| 1458235 | 12/1976 | United Kingdom | 21/2.7 A |

OTHER PUBLICATIONS

C.A. vol. 68, 1968 96958w.
C.A. vol. 65, 1966, 557(b).
R. Q. Brewster & W. E. McEwen, "Organic Chemistry", 3rd Ed. Prentice-Hall, Englewood Cliffs (1961) 383-384.
Beilstein, vol. 2, pp. 622, 555 and 559 (1932).
A. Streitwieser, Jr. and C. H. Heathcock, "Organische Chemie", Verlag Chemie, Basel, 1980 p. 811.
W. Lossen and E. Mendthal, Ann., 348, 261-263 (1906).
Chem. Abst. 83, 20628r (1975), Hasegawa et al.

*Primary Examiner*—Patricia L. Morris
*Assistant Examiner*—Mary Susan H. Gabilan
*Attorney, Agent, or Firm*—Luther A. R. Hall

[57] ABSTRACT

Compounds of the formula

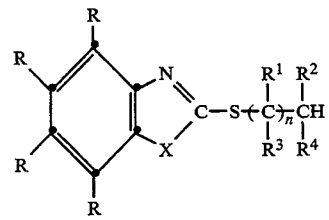

in which X is —S—, —O— or —NH—, R is H or a monovalent substituent, n is 0 or 1 and $R^1$, $R^2$, $R^3$ and $R^4$ are H, alkyl, alkyl which is substituted by OH, halogen, COOH or alkoxy, unsubstituted or substituted aryl or aralkyl, or carboxyl, or $R^1$ and $R^2$ or $R^1$ and $R^3$ together are alkylene or $R^1$ and $R^2$ are a direct bond, at least two of the groups $R^1$, $R^2$, $R^3$ and $R^4$ being carboxyl or carboxyalkyl groups, and base addition salts thereof are effective corrosion inhibitors. The preparation of these novel polycarboxylic acids can be effected by various processes.

8 Claims, No Drawings

THIO(CYCLO) ALKANEPOLYCARBOXYLIC ACIDS CONTAINING HETEROCYCLIC SUBSTITUENTS

This is a continuation of application Ser. No. 07/348,096, filed on May 3, 1989, now abandoned, which is a continuation of application Ser. No. 06/865,946, filed on May 19, 1986, now abandoned, which is a continuation of application Ser. No. 06/610,146, filed on May 14, 1984, now abandoned.

The present invention relates to novel thio(cyclo)alkanepolycarboxylic acids which contain heterocyclic substituents and can be used as corrosion inhibitors. These are benzoxazole-2-thiopolycarboxylic acids, benzthiazole-2-thiopolycarboxylic acids and benzimidazole-2-thiopolycarboxylic acids.

U.S. Pat. No. 2,725,364 describes esters of benzthiazol-2-ylthiosuccinic acid which have the formula

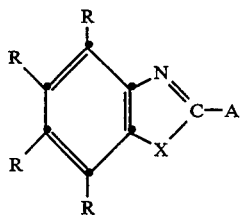

(II)

in which R° is a hydrocarbon radical or oxahydrocarbon radical having 3-12 C atoms, and which can be used as plasticities for vinylchloride polymers. Their preparation is effected by base-catalysed addition of maleic acid esters onto 2-mercaptobenzthiazole. It is mentioned that the esters can also be prepared by esterifying the corresponding dicarboxylic acid (R°=H) and that this dicarboxylic acid can be obtained by addition of maleic or fumaric acid onto 2-mercaptobenzthiazole in an aqueous alkaline medium. However, no details of the properties and preparation of this dicarboxylic acid are described therein. Our own experiments have shown that 2-mercaptobenzthiazole does not react with maleic acid in an aqueous alkaline medium. Our own experiments have also shown that benzthiazol-2-ylthiosuccinic acid prepared by another route undergoes slow cleavage into 2-mercaptobenzthiazole and fumaric acid in an aqueous alkaline medium at 45°-50° C.

It has been found, however, that this dicarboxylic acid and similar heterocyclic mercaptocarboxylic acids can be prepared by another means. The compounds concerned here are those of the formula I

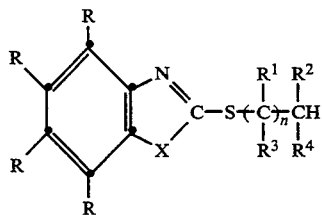

I in which each R independently of the others is hydrogen, alkyl, halogenoalkyl, alkoxy, alkylthio, alkylsulfonyl, phenyl, alkylphenyl, phenylalkyl, cycloalkyl, halogen, —NO₂, —CN, —COOH, —COOalkyl, —OH or a primary, secondary or tertiary amino or carbamoyl group, X is —O—, —S— or —NH—, n is zero or 1, and, if n is 1, R¹, R², R³ and R⁴ independently of one another are hydrogen, alkyl, hydroxyalkyl, carboxyalkyl, halogenoalkyl, alkoxyalkyl, carboxyl or unsubstituted or substituted aryl or aralkyl, or R¹ and R² or R¹ and R³ together are linear or branched alkylene which can be substituted by 1 or 2 carboxyl groups, or R¹ and R² together are a direct bond, and, if n is 0, R²and R⁴ are carboxyl, subject to the proviso that the group

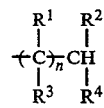

contains at least two and not more than four carboxyl groups and that, in the event that X is NH and three of the radicals R are hydrogen, the group —C(R¹)(R³)—CH(R²)(R⁴) is not a 1, dicarboxyethyl group, and also base addition salts of these compounds.

The compounds concerned are, in particular, those of the formula I in which each R independently of the others is H, C₁-C₁₂-alkyl, C₁-C₄-halogenoalkyl, C₁-C₁₂-alkoxy, C₁-C₁₂-alkylthio, C₁-C₁₂-alkylsulfonyl, phenyl, C₇-C₁₆-alkylphenyl, C₇-C₁₆-phenylalkyl, C₅-C₈-cycloalkyl, halogen, —NO₂, —CN, —COOH, —COO(C₁-C₄-alkyl), —OH or a primary, secondary or tertiary amino or carbamoyl group having up to 20 C atoms, X is —O—, —S— or —NH—, n is zero or 1, and, if n is 1, R¹, R² R³ and R⁴ independently of one another are H, C₁-C₁₈-alkyl, C₁-C₄-hydroxyalkyl, C₂-C₁₂-carboxyalkyl, C₁-C₄-halogenoalkyl, C₂-C₁₀-alkoxyalkyl, —COOH or aryl or aralkyl having 6°-10 C atoms which is unsubstituted or substituted by C₁-C₄-alkyl, C₁-C₄-alkoxy, —NO₂, —COOH, —OH or halogen, or R¹ and R² or R¹ and R³ together are linear or branched C₃-C₈-alkylene which can be substituted by 1 or 2 carboxyl groups, or R¹ and R² together are a direct bond, and, if n is 0, R² and R⁴ are carboxyl, subject to the proviso that the group

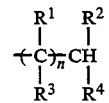

contains at least two and not more than four carboxyl groups and that, in the event that X is NH and three of the radicals R are hydrogen, the group —C(R¹)(R³)—CH(R²)(R⁴) is not a 1,2-dicarboxyethyl group, and also base addition salts of these compounds.

If X in formula I is —O—, these are benzoxazole derivatives. If X is —NH—, they are benzimidazole derivatives. If X is —S—, they are benzthiazole derivatives. The latter are preferred. Compounds of the formula I in which n is 1 are also preferred.

As alkyl, R can be, for example, methyl, ethyl, propyl, isopropyl, n-butyl, isobutyl, tert.-butyl, n-pentyl, isopentyl, n-hexyl, 2-ethylbutyl, n -heptyl, n-octyl, 1,1,3,3-tetramethylbutyl, n-nonyl, isononyl, n-decyl, n-undecyl or n-dodecyl. As halogenoalkyl, R can be, for example, chloromethyl, trichloromethyl, monofluoromethyl, difluoromethyl, trifluoromethyl or 2-chloroethyl. As alkoxy, R can be, for example, methoxy, ethoxy, propoxy, isopropoxy, butoxy, hexyloxy, octyloxy or dodecyloxy. As alkylthio, R can be, for example, methylthio, ethylthio, isopropylthio, n-butylthio, tert.-butylthio, n-hexylthio or n-dodecylthio.

As alkylsulfonyl, R can be, for example, methylsulfonyl, tert.-butylsulfonyl, n-octylsulfonyl, 2-ethylhexylsulfonyl or n-dodecylsulfonyl. As alkylphenyl, R can be, for example, tolyl, xylyl, ethylphenyl, tert.-butylphenyl, hexylphenyl or nonylphenyl. As phenylalkyl, R can be, for example, benzyl, 1-phenylethyl, 2-phenylethyl or 1-phenylbutyl. As cycloalkyl, R can be, for example, cyclopentyl, cyclohexyl or cyclooctyl. As —COOalkyl, R can be, for example, methoxycarbonyl, ethoxycarbonyl, isopropoxycarbonyl or butoxycarbonyl. As halogen, R can be, for example, fluorine, chlorine or bromine. As a primary, secondary or tertiary amino group, R can be, for example, an amino, isopropylamino, anilino, tert.-butylamino, dimethylamino, diethylamino, dipropylamino, di-(hydroxyethyl)-amino, dibutylamino, dioctylamino, cyclohexylamino, N-methylanilino, N-methylbenzylamino, piperidino or morpholino group. As a primary, secondary or tertiary carbamoyl group, R can be, for example, —CONH$_2$, —CONHCH$_3$, —CONHphenyl, —CONHcyclohexyl, —CON(CH$_3$)$_2$, —CON(C$_6$H$_{13}$)$_2$ or morpholinocarbonyl or piperidinocarbonyl.

Preferably, one of the substituents R is hydrogen, C$_1$–C$_4$-alkyl, C$_1$–C$_4$-alkoxy or amino and the other three Rs are H. It is particularly preferable for all four Rs to be hydrogen.

As alkyl, R$^1$, R$^2$, R$^3$ and R$^4$ can be, for example, methyl, ethyl, n-propyl, isopropyl, n-butyl, isobutyl, n-pentyl, n-hexyl, n-octyl, isooctyl, n-decyl, n-dodecyl, n-hexadecyl or n-octadecyl. As hydroxyalkyl or alkoxyalkyl, R$^1$, R$^2$, R$^3$ and R$^4$ can be, for example, hydroxymethyl, 1-hydroxyethyl, 2-hydroxyethyl, 2-hydroxypropyl, 3-hydroxypropyl, 2-hydroxybutyl, 2-methoxyethyl, isopropoxymethyl, 2-butoxyethyl, octyloxymethyl, 2-ethoxypropyl or 3-methoxypropyl. As halogenoalkyl, R$^1$, R$^2$, R$^3$ and R$^4$ can be, for example, fluoroalkyl or chloroalkyl, for example monofluoromethyl, difluoromethyl, trifluoromethyl, chloromethyl or 2-chloroethyl. As carboxyalkyl, R$^1$R$^2$, R$^3$and R$^4$ can be monocarboxyalkyl, dicarboxyalkyl or tricarboxyalkyl, for example carboxymethyl, 1-carboxyethyl, 2-carboxyethyl, 1-, 2- or 3-carboxypropyl, 1-carboxyisopropyl, 4-carboxybutyl, 6-carboxyhexyl, 11-carboxyundecyl, 1,2-dicarboxyethyl, 2,3-dicarboxypropyl or 2,3,4-tricarboxylbutyl. As unsubstituted or substituted aryl or aralkyl, R$^1$, R$^2$, R$^3$ and R$^4$ can be, for example, phenyl, tolyl, xylyl, 4-isopropylphenyl, 3-methoxyphenyl, 4-ethoxyphenyl, 3-nitrophenyl, 3-carboxyphenyl, 3,4-dicarboxyphenyl, 4-chlorophenyl, 2-bromophenyl, 3-hydroxyphenyl, 4-hydroxyphenyl, naphthyl, chloronaphthyl, nitronaphthyl, hydroxynaphthyl, methylnaphthyl, benzyl, 4-methylbenzyl, 3-chlorobenzyl, 4-hydroxybenzyl, α,α-dimethylbenzyl, 2-phenylethyl or 2-phenylpropyl.

If R$^1$ and R$^2$ or R$^1$ and R$^3$ together are alkylene, they form, together with the C atoms to which they are attached, a cycloaliphatic ring, in particular a cyclopentane or cyclohexane ring which can be substituted by lower alkyl groups and by 1 or 2 carboxyl groups.

If R$^1$ and R$^2$ together are a direct bond, the compounds of the formula I are unsaturated polycarboxylic acids.

In the event that n is 0, R$^2$ and R$^4$ are carboxyl. In the event that n is 1, at least two of the substituents R$^1$, R$^2$, R$^3$and R$^4$ carboxyl or carboxyalkyl. Preferably, R$^1$, R$^2$, R$^3$ and R$^4$ independently of one another are H, C$_1$–C$_{12}$-alkyl, C$_1$–C$_4$-hydroxyalkyl, C$_2$–C$_6$-carboxyalkyl, C$_2$–C$_{10}$-alkoxyalkyl, carboxyl, phenyl or benzyl, or R$^1$ and R$^2$ together are trimethylene or tetramethylene. It is particularly preferable for R$^1$, R$^2$, R$^3$ and R$^4$ to be hydrogen, C$_1$–C$_4$-alkyl, carboxyl or C$_2$–C$_6$-carboxyalkyl. Compounds in which two of the substituents R$^1$, R$^2$, R$^3$ and R$^4$ are carboxyl or carboxyalkyl are also preferred.

On the basis of this definition, the group

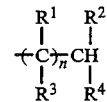

is a di-, tri- or tetra-carboxylic acid group, preferably a dicarboxylic acid group. Examples of such groups are: dicarboxymethyl, 1,2-dicarboxyethyl, 1,2-dicarboxyethenyl, 1,2-dicarboxypropyl, 2,3-dicarboxypropyl, 1,3-dicarboxy-2-propyl, 1,3-dicarboxypropyl, 1,2-dicarboxyprop-1-enyl, 2,3-dicarboxy-1-phenylpropyl, 2,3-dicarboxy-1,1-diphenylpropyl, 2,3-dicarboxy-1-(carboxyphenyl)-propyl, 2,3-dicarboxy-1-(2,4-dicarboxyphenyl)-propyl, 1,2-dicarboxy-2-methylpropyl, 2,3-dicarboxy-2-butyl, 1,2- dicarboxybutyl, 2,4-dicarboxybutyl, 3,4-dicarboxybutyl, 1,4-dicarboxybutyl, 3,4-dicarboxy-3-hexyl, 1,2,3-tricarboxypropyl, 2,3,4-tricarboxybutyl, 1,1,2,2-tetracarboxyethyl, 2,4,6,8-tetracarboxyoctyl and 1,2, 2,3- or 3,4-dicarboxycyclohexyl.

The base addition salts of these compounds are preferably salts of alkali metals, alkaline earth metals or metals of group IIB, IIIA or VIII of the periodic system or salts of ammonia or organic amines, in particular sodium, potassium, calcium, magnesium, zinc, aluminium, ammonium salts or salts of primary, secondary or tertiary amines, for example methylamine, ethanolamine, diethylamine, dibutylamine, diethanolamine, cyclohexylamine, trimethylamine, tri(isopropyl)amine, trioctylamine, triethanolamine or technical mixtures of amines.

The following are examples of individual compounds of the formula I: benzthiazol-2-ylthiomalonic acid, benzthiazol-2-ylthiosuccinic acid, 5-methylbenzthiazol-2-ylthiosuccinic acid, 5-trifluoromethylbenzthiazol-2-ylthiosuccinic acid, 6-ethylbenzthiazol-2-ylthiosuccinic acid, 4-isopropylbenzthiazol-2-ylthiosuccinic acid, 7-t-butylbenzthiazol-2-ylthiosuccinic acid, 5-n-hexylbenzthiazol-2-ylthiosuccinic acid, 6-[1,1,3,3-tetramethylbutyl]-benzthiazol-2-ylthiosuccinic acid, 6-cyclohexylbenzthiazol-2-ylthiosuccinic acid, 7-benzylbenzthiazol-2-ylthiosuccinic acid, 6-methoxybenzthiazol-2-ylthiosuccinic acid, 6-ethoxybenzthiazol-2-ylthiosuccinic acid, 7-ethoxybenzthiazol-2-ylthiosuccinic acid, 5-methoxybenzthiazol-2-ylthiosuccinic acid, 4-methylthiobenzthiazol-2-ylthiosuccinic acid, 4-fluorobenzthiazol-2-ylthiosuccinic acid, 5-chlorobenzthiazol-2-ylthiosuccinic acid, 7-bromobenzthiazol-2-ylthiosuccinic acid, 6-chlorobenzthiazol-2-ylthiosuccinic acid, 4-phenylbenzthiazol-2-ylthiosuccinic acid, 6-nitrobenzthiazol-2-ylthiosuccinic acid, 5-carboxybenzthiazol-2-ylthiosuccinic acid, 5-ethoxycarbonylbenzthiazol-2-ylthiosuccinic acid, 7-hydroxybenzthiazol-2-ylthiosuccinic acid, 5-chloro-6-n-butylbenzthiazol-2-ylthiosuccinic acid, 5-bromo-5-n-hexylbenzthiazol-2-ylthiosuccinic acid, 5-nitro-6-n-propylbenzthiazol-2-ylthiosuccinic acid, 5-cyanobenzthiazol-2-ylthiosuccinic acid, 5-bromo-6-n-propoxybenzthiazol-2-ylthiosuccinic acid, 6-aminobenzthiazol-2-ylthiosuccinic acid, 6-methylaminobenzthiazol-2-ylsuccinic acid, 6-dimethylaminobenzthiazol-2-ylsuccinic acid, 7-phenylaminobenzthiazol-2-ylsuccinic acid, 4-dibenzylaminobenzthiazol-2-ylsuccinic acid, 4-morpholinobenzthiazol-2-ylsuccinic acid, 5-carbamoylbenzthiazol-2-ylsuccinic acid, 5-methylcarbamoylbenzthiazol-2-ylsuccinic acid, 5-diethylcarbamoylbenzthiazol-2-ylsuccinic acid, 6-phenylcarbamoylbenzthiazol-2-ylsuccinic acid, 5,6-dimethylbenzthiazol-2-ylthiosuccinic acid, 4,5,6-triethylbenzthiazol-2-ylthiosuccinic acid, 4,5,6,7-tetramethylbenzthiazol-2-ylthiosuccinic acid, 1-(benzthiazol-2-ylthio)-propane-1,2-dicarboxylic acid, 1-(4-phenylbenzthiazol-2-ylthio)-propane-1,2-dicarboxylic acid, 3-(benzthiazol-2-ylthio)-propane-1,2-dicarboxylic acid, 3-(6-trifluoromethylbenzthiazol-2-yl)-propane-1,2-dicarboxylic acid, 3-(6-methoxycarbonylbenzthiazol-2-yl)-propane-1,2-dicarboxylic acid, 3-(6-aminobenzthiazol- 2-yl)-propane-1,2-dicarboxylic acid, 3-(4-morpholinobenzthiazol-2-yl)-propane-1,2-dicarboxylic acid, 1-(benzthiazol-2-ylthio)-propane-1,3-dicarboxylic acid, 1-(6-ethylthiobenzthiazol-2-ylthio)-propane-1,3-dicarboxylic acid, 2-(benzthiazol-2-ylthio)-propane-1,3-dicarboxylic acid, 2-(5-carboxy-benzthiazol-2-ylthio)-propane-1,3-dicarboxylic acid, 3-(benzthiazol-2-ylthio)-3-phenylpropane-1,2-dicarboxylic acid, 3-(benzthiazol-2-ylthio)-3-(4-carboxyphenyl)-propane-1,2-dicarboxylic acid, 3-(benzthiazol-2-ylthio)-3-(2,4-dicarboxyphenyl)-propane-1,2-dicarboxylic acid, 3-(benzthiazol-2-ylthio)-3,3-diphenylpropane-1,2-dicarboxylic acid, 1-(benzthiazol-2-ylthio)-butane-1,2-dicarboxylic acid, 1-(4-methoxy-6-hydroxybenzthiazol-2-ylthio)-butane-1,2-dicarboxylic acid, 1-(benzthiazol-2-ylthio)-propane-2,3-dicarboxylic acid, 1-(4,5-dimethyl-7-propoxybenzthiazol-2-ylthio)-propane-2,3-dicarboxylic acid, 1-(benzthiazol-2-ylthio)-2-methylpropane-1,2-dicarboxylic acid, 2-(benzthiazol-2-ylthio)-butane-2,3-dicarboxylic acid, 1-(benzthiazol-2-ylthio)-butane-2,4-dicarboxylic acid, 4-(benzthiazol-2-ylthio)-butane-1,2,3-tricarboxylic acid, 4-(benzthiazol-2-ylthio)-butane-1,4-dicarboxylic acid, 1-(benzthiazol-2-ylthio)-pentane-1,5-dicarboxylic acid, 1-(benzthiazol-2-ylthio)-hexane-1,6-dicarboxylic acid, 4-(benzthiazol-2-ylthio)-cyclohexane-1,2-dicarboxylic acid, 1-(benzthiazol-2-ylthio)-cyclohexane-1,2-dicarboxylic acid, 1-(benzthiazol-2-ylthio)-propane-1,2,3-tricarboxylic acid, 3-(benzthiazol-2-ylthio)-3-chloropropane-1,3-dicarboxylic acid, 1-(benzthiazol-2-ylthio)-3-methoxypropane-1,2-dicarboxylic acid, 1-(benzthiazol-2-ylthio)-3-hydroxypropane-1,2-dicarboxylic acid, 1-(benzthiazol-2-ylthio)-2-phenylsuccinic acid, 1-(benzthiazol-2-ylthio)-2-benzylsuccinic acid, 1-(benzthiazol-2-ylthio)-3-methylbutane-1,3-dicarboxylic acid, 3-(benzthiazol-2-ylthio)-hexane-3,4-dicarboxylic acid, benzoxazol-2-ylthiomalonic acid, benzoxazol-2-ylthiosuccinic acid, 5-methylbenzoxazol-2-ylthiosuccinic acid, 6-ethylbenzoxazol-2-ylthiosuccinic acid, 4-isopropylbenzoxazol-2-ylthiosuccinic acid, 4-t-butylbenzoxazol-2-ylthiosuccinic acid, 5-n-hexylbenzoxazol-2-ylthiosuccinic acid, 6-[1,1,3,3-tetramethylbutyl]-benzoxazol-2-ylthiosuccinic acid, 6-cyclohexylbenzoxazol-2-ylthiosuccinic acid, 7-benzylbenzoxazol-2-ylthiosuccinic acid, 6-methoxybenzoxazol-2-ylthiosuccinic acid, 6-ethoxybenzoxazol-2-ylthiosuccinic acid, 7-ethoxybenzoxazol-2-ylthiosuccinic acid 5-methoxybenzoxazol-2-ylthiosuccinic acid, 4-methyl thiobenzoxazol-2-ylthiosuccinic acid, 6-methylsulfonylbenzoxazol-2-ylthiosuccinic acid, 4-fluorobenzoxazol-2-ylthiosuccinic acid, 5-chlorobenzoxazol-2-ylthiosuccinic acid, 7-bromobenzoxazol-2-ylthiosuccinic acid, 6-chlorobenzoxazol-2-ylthiosuccinic acid, 4-phenylbenzoxazol-2-ylthiosuccinic acid, 6-nitrobenzoxazol-2-ylthiosuccinic acid, 5-cyanobenzoxazol-2-ylthiosuccinic acid, 5-carboxybenzoxazol-2-ylthiosuccinic acid, 5-ethoxycarbonylbenzoxazol-2-ylthiosuccinic acid, 7-hydroxybenzothiazol-2-ylthiosuccinic acid, 5-chloro-6-n-butylbenzoxazol-2-ylthiosuccinic acid, 4-bromo-5-n-hexylbenzoxazol-2-ylthiosuccinic acid, 5-nitro-6-n-propylbenzoxazol-2-ylthiosuccinic acid, 5-bromo-6-n-propoxybenzoxazol-2-ylthiosuccinic acid, 6-aminobenzoxazol-2-ylthiosuccinic acid, 5-dimethylaminobenzoxazol-2-ylthiosuccinic acid, 4-benzylaminobenzoxazol-2-ylthiosuccinic acid, 4-piperidinobenzoxazol-2-ylthiosuccinic acid, 5-carbamoylbenzoxazol-2-ylthiosuccinic acid, 5-dimethylcarbamoylbenzoxazol-2-ylthiosuccinic acid, 6-phenylcarbamoylbenzoxazol-2-ylthiosuccinic acid, 5,6-dimethylbenzoxazol-2-ylthiosuccinic acid, 4,5,6-triethylbenzoxazol-ylthiosuccinic acid, 4,5,6,7-tetramethylbenzoxazol-2-ylthiosuccinic acid, 1-(benzoxazol-2-ylthio)-propane-1,2-dicarboxylic acid, 1-(4-phenylbenzoxazol-2-ylthio)-propane-1,2-dicarboxylic acid, 3-(benzoxazol-2-ylthio)-propane-1,2-dicarboxylic acid, 3-(6-aminobenzoxazol-2-ylthio)-propane-1,2-dicarboxylic acid, 3-(6-methoxycarbonylbenzoxazol-2-ylthio)-propane-1,2-dicarboxylic acid, 3-(6-trifluoromethylbenzoxazol-2-ylthio)-2-propane-1,2-dicarboxylic acid, 1-(benzoxazol-2-ylthio)-propane-1,3-dicarboxylic acid, 1-(6-ethylthiobenzoxazol-2-ylthio)-propane-1,3-dicarboxylic acid, 2-(benzoxazol-2-ylthio)-propane-1,3-dicarboxylic acid, 2-(5-carboxybenzoxazol-2-ylthio)-propane-1,3-dicarboxylic acid, 3-(benzoxazol-2-ylthio)-3-phenylpropane-1,2-dicarboxylic acid, 3-(benzoxazol- 2-ylthio)-3-(4-carboxyphenyl)-propane-1,2-dicarboxylic acid, 1-(benzoxazol-2-ylthio)-butane-1,2-dicarboxylic acid, 1-(4-methoxy-6-hydroxybenzoxazol-2-ylthio)-butane-1,2-dicarboxylic acid, 1-(4,5-dimethyl-7-propoxybenzoxazol-2-ylthio)-propane-2,3-dicarboxylic acid, 1-(benzoxazol-2-ylthio)-2-methylpropane-1,2-dicarboxylic acid, 2-(benzoxazol-2-ylthio)-butane-2,3-dicarboxylic acid, 1-(benzoxazol-2-ylthio)-butane-2,4-dicarboxylic acid, 4-(benzoxazol-2-ylthio)-butane-1,4-dicarboxylic acid, 4-(benzoxazol-2-ylthio)-butane-1,2,3-tricarboxylic acid, 1-(benzoxazol-2-ylthio)-pentane-1,5-dicarboxylic acid, 4-(benzoxazol-2-ylthio)-cyclohexane-1,2-dicarboxylic acid, 1-(benzoxazol-2-ylthio)-cyclohexane-1,2-dicarboxylic acid, 1-(benzoxazol-2-ylthio)-propane-1,2,3-tricarboxylic acid, 3-(benzoxazol-2-ylthio)-3-chloropropane-1,3-dicarboxylic acid, 1-(benzoxazol-2-ylthio)-3-methoxypropane-1,2-dicarboxylic acid, 1-(benzoxazol-2-ylthio)-3-hydroxypropane-1,2-dicarboxylic acid, 1-(benzoxazol-2-ylthio)-2-phenylsuccinic acid, 1-(benzoxazol-2-ylthio)-2-benzylsuccinic acid, 1-(benzoxazol-2-ylthio)-3-methylbutane-1,3-dicarboxylic acid, 3-(benzoxazol-2-ylthio)-hexane-3,4-dicarboxylic acid, benzimidazol-2-ylthiomalonic acid, 5-(or 6)-chloro-6-(or 5)-n-butylbenzimidazol-2-ylthiosuccinic acid, 4-(or 7)-bromo-5-(or 6)-n-hexylbenzimidazol-2-ylthiosuccinic acid, 5-trifluoromethyl-6-aminobenzimidazol-2-ylthiosuccinic acid, 5-(or 6)-nitro-6-(or 5)-n-propylbenzimidazol-2-ylthiosuccinic acid, 5-(or 6)-bromo-6-(or 5)-n-propoxybenzimidazol-2-ylthiosuccinic acid, 5,6-dimethylbenzimidazol-2-ylthiosuccinic acid, 4,5,6-triethylbenzimidazol-2-ylthiosuccinic acid, 4,5,6,7-tetramethylbenzimidazol-2-ylthiosuccinic acid, 1-(benzimidazol-2-ylthio)-propane-1,2-dicarboxylic acid, 3-(benzimidazol-2-ylthio)-propane-1,2-dicarboxylic acid, 3-(5-aminobenzimidazol-2-ylthio)-propane-1,2-dicarboxylic acid, 3-(6-ethoxycarbonylbenzimidazol-2-ylthio)-propane-1,2-dicarboxylic acid, 3-(4-morpholinobenzimidazol-2-ylthio)-propane-1,2-dicarboxylic acid, 3-(5-carbamoylbenzimidazol-2-ylthio)-propane-1,2-dicarboxylic acid, 3-(7-cyanobenzimidazol-2-ylthio)-propane-1,2-dicarboxylic acid, 1-(4-(or 7)-phenylbenzimidazol-2-ylthio) propane-1,2-dicarboxylic acid, 1-(benzimidazol-2-ylthio)-propane-1,3-dicarboxylic acid, 1-(6-(or 5)-ethylthiobenzimidazol-2-ylthio)-propane-1,3-dicarboxylic acid, 2-(benzimidazol-2-ylthio)-propane-1,3-dicarboxylic acid, 2-(5-(or 6)-carboxybenzimidazol-2-ylthio)-propane-1,3-dicarboxylic acid, 3-(benzimidazol-2-ylthio)-3-phenylpropane-1,2-dicarboxylic acid, 3-(benzimidazol-2-ylthio)-3-(2,4-dicarboxyphenyl)-propane-1,2-dicarboxylic acid, 1-(benzimidazol-2-ylthio)-butane-1,2-dicarboxylic acid, 1-(4 or 7)-methoxy-6-(or 5)-hydroxybenzimidazol-2-ylthiobutane-1,2-dicarboxylic acid, 4-(benzimidazol-2-ylthio)-butane-1,2,3-tricarboxylic acid, 1-(benzimidazol-2-ylthio)-propane-2,3-dicarboxylic acid, 1-(4 or 7)-methyl-7-(or 4)-propoxybenzimidazol-2-ylthio-propane-2,3-dicarboxylic acid, 1-(benzimidazol-2-ylthio)-2-methylpropane-1,2-dicarboxylic acid, 2-(benzimidazol-2-ylthio)-butane-2,3-dicarboxylic acid, 1-(benzimidazol-2-ylthio)-butane-2,4-dicarboxylic acid, 4-(benzimidazol-2-ylthio)-butane-1,4-dicarboxylic acid, 3-(benzimidazol-2-ylthio)-hexane-1,2-dicarboxylic acid, 1-(benzimidazol-2-ylthio)-cyclohexane-1,2-dicarboxylic acid, 1-(benzimidazol-2-ylthio)-propane-1,2,3-tricarboxylic acid, 3-(benzimidazol-2-ylthio)-3-carboxy-4-chloropropane-1,3-dicarboxylic acid, 1-(benzimidazol-2-ylthio)-3-methoxypropane-1,2-dicarboxylic acid, 1-(benzimidazol-2-ylthio)-3-hydroxypropane-1,2-dicarboxylic acid, 1-(benzimidazol-2-ylthio)-2-phenylsuccinic acid, 1-(benzimidazol-2-ylthio)-2-benzylsuccinic acid, 1-(benzimidazol-2-ylthio)-3-methylbutane-1,3-dicarboxylic acid and 3-(benzimidazol-2-ylthio)-hexane-3,4-dicarboxylic acid and the base addition salts of these compounds, for example the sodium, potassium, calcium, magnesium, zinc, cobalt, aluminium, ammonium, mono-, di- and trialkylammonium, cyclohexylammonium or trishydroxyethylammonium salts.

The compounds of the formula I can be prepared by reacting a compound of the formula II

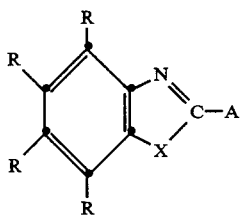

in which R and X are as defined above and A is a leaving group, for example Cl, Br, I or benzenesulfonyloxy or p-toluenesulfonyloxy, with a compound of the formula III

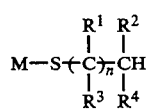

in which n, $R^1$, $R^2$, $R^3$ and $R^4$ are as defined above and M is hydrogen or a cation, for example an alkali metal cation, alkaline earth metal cation or a substituted or unsubstituted ammonium cation.

Alternatively, a compound of the formula IV

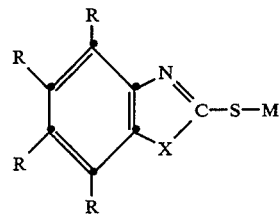

can be reacted with a compound of the formula V

These reactions can be carried out in customary manner in the presence of an organic or inorganic base. Examples of such bases are tertiary amines, ammonium hydroxide, sodium methoxide, sodium hydroxide, potassium hydroxide or sodium carbonate. If a corresponding excess of the base is used, the product of the formula I is initially obtained in the form of the base salt, and the free carboxylic acid can be obtained therefrom by neutralisation with an acid.

The reactions can be carried out in an organic solvent, for example in methanol, ethanol, acetonitrile, toluene, chloroform, dimethyl sulfoxide or dimethylformamide. It is preferable to carry out the react ion in an aqueous alkaline medium, for example in aqueous $Na_2CO_3$ solution or NaOH solution. The product can then be isolated by adding a mineral acid.

The reactions can be carried out at room temperature or an elevated temperature; the reaction is preferably carried out at 50° to 100° C.

Certain compounds of the formula I can be converted into other compounds of the formula I by known processes. For example, a compound having a nitro group in the benzo radical can be converted by hydrogenation into the corresponding amino compound.

The following are examples of compounds of the formula II: 5-methyl-2-bromobenzthiazole, 6-ethyl-2-chlorobenzthiazole, 4-isopropyl-2-iodobenzthiazole, 7-t-butyl-2-bromobenzthiazole, 5-n-hexyl-2-bromobenzthiazole, 6-(1,1,3,3-tetramethylbutyl)-2-chlorobenzthiazole, 6-cyclohexyl-2-iodoenzthiazole, 7-benzyl-2-chlorobenzthiazole, 5-trifluoromethyl-2-chlorobenzthiazole, 6-methoxy-2-toluenesulfonyloxybenzthiazole, 6-ethoxy-2-chlorobenzthiazole, 7-ethoxy-2-chlorobenzthiazole, 5-methoxy-2- iodobenzthiazole, 5-ethoxycarbonyl-2-bromobenzthiazole, 4-methylthio-2-bromobenzthiazole, 6-isopropoxy-2-chlorobenzthiazole, 5-cyano-2-chlorobenzthiazole, 4-fluoro-2-chlorobenzthiazole, 5-chloro-2-bromobenzthiazole, 6-chloro-2-iodobenzthiazole, 4-phenyl-2-chlorobenzthiazole, 6-nitro-2-chlorobenzthiazole, 6-methylsulfonyl-2-chlorobenzthiazole, 5-carboxy-2-iodobenzthiazole, 7-hydroxy-2-chlorobenzthiazole, 6-amino-2-chlorobenzthiazole, 5-chloro-6-n-butyl-2-bromobenzthiazole, 4-bromo-5-n-hexyl-2-chlorobenzthiazole, 5-nitro-6-n-propyl-2-chlorobenzthiazole, 5-bromo-6-n-propoxy-2-iodobenzthiazole, 4-nitro-7-butyl-2-chlorobenzthiazole, 4,5,6-triethyl-2-bromobenzthiazole, 4,5,6,7-tetramethyl-2-chlorobenzthiazole, 4-methoxy-6-hydroxy-2-chlorobenzthiazole, 4,5-dimethyl-7- propoxy-2-indobenzthiazole, 5-dimethylamino-2-bromobenzthiazole, 4-morpholino-2-chlorobenzthiazole, 5-diethylcarbamoyl-2-bromobenzthiazole, 6-phenylcarbamoyl-2-chlorobenzthiazole, 5-methyl-2-bromobenzimidazole, 6-ethyl-2-chlorobenzimidazole, 4-isopropyl-2-iodobenzimidazole, 5-trifluoromethyl-3-chlorobenzimidazole, 7-t-butyl-2-bromobenzimidazole, 5-n-hexyl-2-bromobenzimidazole, 6-(1,1,3,3-tetramethylbutyl)-2-chloro-benzimidazole, 6-cyclohexyl-2-iodobenzimidazole, 7-benzyl-2-chlorobenzimidazole, 6-methoxy-2-toluenesulfonyloxybenzimidazole, 6-ethoxy-2-chlorobenzimidazole, 7-ethoxy-2-chlorobenzimidazole, 5-methoxy-2-iodobenzimidazole, 4-methylthio-2-bromobenzimidazole, 6-isopropoxy-2-chlorobenzimidazole, 4-fluoro-2-chlorobenzimidazole, 5-chloro-2-bromobenzimidazole, 6-chloro-2-iodobenzimidazole, 4-phenyl-2-chlorobenzimidazole, 6-nitro-2-chlorobenzimidazole, 5-amino-2-chlorobenzimidazole, 5-carbamoyl-2-chlorobenzimidazole, 5-carboxy-2-iodobenzimidazole, 7-hydroxy-2-chlorobenzimidazole, 5-chloro-6-n-butyl-2-bromobenzimidazole, 4-bromo-5-n-hexyl-2-chlorobenzimidazole, 5-nitro-6-n-propyl-2-chlorobenzimidazole, 5-bromo-6-n-propoxy-2-iodobenzimidazole, 4-nitro-7-butyl-2-chlorobenzimidazole, 4,5,6-triethyl-2-bromobenzimidazole, 4,5,6,7-tetramethyl-2-chlorobenzimidazole, 4-methoxy-6-hydroxy-2-chlorobenzimidazole, 4,5-dimethyl-7-propoxy-2-iodobenzimidazole, 5- (or 6)-chloro-6-(or 5)-n-butyl-2-bromobenzimidazole, 4-(or 7)-bromo-5-(or 6)-n-hexyl-2-iodobenzimidazole, 5-(or 6)-nitro-6- (or 5)-n-propyl-2-chlorobenzimidazole, 5-(or 6)-bromo-6-(or 5)-n-propoxy-2-iodobenzimidazole, 4-(or 7)-nitro-7-(or 4)-butyl-2-chlorobenzimidazole, 4-(or 7)-, 5-(or 6)-, 6-(or 5)-triethyl-2-bromobenzimidazole, 4,5,6,7-tetramethyl-2-bromobenzimidazole, 4-(or 7)-methoxy-6-(or 5)-hydroxy-2-chlorobenzimidazole, 4-(or 7)-, 5-(or 6)-dimethyl-7-(or 4)-propoxy- 2-chlorobenzimidazole, 5-methyl-2-bromobenzoxazole, 6-ethyl-2-chlorobenzoxazole, 4-isopropyl-2-iodobenzoxazole, 7-t-butyl-2-bromobenzoxazole, 5-n-hexyl-2-bromobenzoxazole, 6-(1,1,3,3-tetramethylbutyl)-2-chlorobenzoxazole, 6-cyclohexyl-2-iodobenzoxazole, 7-benzyl-2-chlorobenzoxazole, 6-methoxy-2-totuenesulfonyloxybenzoxazole, 6-ethoxy-2-chlorobenzoxazole, 7-ethoxy-2-chlorobenzoxazole, 5-methoxy-2-iodobenzoxazole, 4-methylthio-2-bromobenzoxazole, 6-isopropoxy-2-chlorobenzoxazole, 4-fluoro-2-chlorobenzoxazole, 5-chloro-2-bromobenzoxazole, 6-chloro-2-iodobenzoxazole, 5-trifluoromethyl-2-chlorobenzoxazole, 4-phenyl-2-chlorobenzoxazole, 6-nitro-2-chlorobenzoxazole, 5-carboxy-2-iodobenzoxazole, 5-methoxycarbonyl-2-chlorobenzoxazole, 5-tert.-butylsulfonyl-2-chlorobenzoxazole, 6-dimethylamino-2-chlorobenzoxazole, 4-morpholino-2-chlorobenzoxazole, 5-diethylcarbamoyl-2-bromobenzoxazole, 7-hydroxy-2-chlorobenzoxazole, 5-chloro-6-n-butyl-2-bromobenzoxazole, 4-bromo-5-n-hexyl-2-iodobenzoxazole, 5-nitro-6-n-propyl-2-chlorobenzoxazole, 5-bromo-6-n-propoxy-2-chlorobenzoxazole, 4-nitro-7-butyl-2-chlorobenzoxazole, 4,5,6-triethyl-2-bromobenzoxazole, 4,5,6,7-tetramethyl-2-chlorobenzoxazole, 4-methoxy-6-hydroxy-2-chlorobenzoxazole and 4,5-dimethyl-7-propoxy-2-iodobenzoxazole.

Examples of reactants of the formula III are mercaptosuccinic acid, the trisodium salt of mercaptosuccinic acid, 2-mercapto-3,3-dimethylsuccinic acid, 2-mercaptoglutaric acid, 3-mercaptoglutaric acid, 2-(mercaptomethyl)-succinic acid, 2-mercapto-3-methylsuccinic acid, 2-mercapto-3-ethylsuccinic acid, 2-(mercaptomethyl)-glutaric acid, 2-mercaptotricarballylic acid, 1-mercaptoethane-1,1,2,2-tetracarboxylic acid, 1-mercaptocyclohexane-1,2-dicarboxylic acid, 2-mercapto-2,3-diethylsuccinic acid, 2-mercapto-3-chloromethylsuccinic acid, 2-mercapto-3-methoxymethylsuccinic acid, 2-mercapto-3-hydroxymethylsuccinic acid, 2-mercapto-3-phenylsuccinic acid and 2-mercapto-3-benzylsuccinic acid.

Examples of compounds of the formula IV are 5-methyl-2-mercaptobenzthiazole, 6-ethyl-2-mercaptobenzthiazole, 4-isopropyl-2-mercaptobenzthiazole, 7-t-butyl-2-mercaptobenzthiazole, 5-n-hexyl-2-mercaptobenzthiazole, 6-(1,1,3,3-tetramethylbutyl)-2-mercaptobenzthiazole, 6-cyclohexyl-2-mercaptobenzthiazole, 7-benzyl-2-mercaptobenzthiazole, 5-trifluoromethyl-2-mercaptobenzthiazole, 6-methoxy-2-mercaptobenzthiazole, 6-ethoxy-2-mercaptobenzthiazole, 7-ethoxy-2-mercaptobenzthiazole, 5-methoxy-2-mercaptobenzthiazole, 4-methylthio-2-mercaptobenzthiazole, 6-methylsulfonyl-2-mercaptobenzthiazole, 6-isopropyl-2-mercaptobenzthiazole, 4-fluoro-2-mercaptobenzthiazole, 5-chloro-2-mercaptobenzthiazole, 7-bromo-2-mercaptobenzthiazole, 6-chloro-2-mercaptobenzthiazole, 4-(phenyl-2-mercapto)-benzthiazole, 6-nitro-2-mercaptobenzthiazole, 5-cyano-2-mercaptobenzthiazole, 5-carboxy-2-mercaptobenzthiazole, 5-methoxycarbonyl-2-mercaptobenzthiazole, 7-hydroxy-2-mercaptobenzthiazole, 6-amino-2-mercaptobenzthiazole, 5-dimethylamino-2-mercaptobenzthiazole, 5-morpholino-2-mercaptobenzthiazole, 5-carbamoyl-2-mercaptobenzthiazole, 5-phenylcarbamoyl-2-mercaptobenzthiazole, 5-chloro-6-n-butyl-2-mercaptobenzthiazole, 4-bromo-5-n-hexyl-2-mercaptobenzthiazole, 5-nitro-6-n-propyl-2-mercaptobenzthiazole, 5-bromo-6-n-propoxy-2-mercaptobenzthiazole, 4-nitro-7-butyl-2-mercaptobenzthiazole, 4,5,6-triethyl-2-mercaptobenzthiazole, 4,5,6,7-tetramethyl-2-mercaptobenzthiazole, 4-methoxy-6-hydroxy-2-mercaptobenzthiazole, 4,5-dimethyl-7-propoxy-2-mercaptobenzthiazole, 5-methyl-2-mercaptobenzimidazole, 6-ethyl-2-mercaptobenzimidazole, 4-isopropyl-2-mercaptobenzimidazole, 7-t-butyl-2-mercaptobenzimidazole, 5-n-hexyl-2-mercaptobenzimidazole, 6-(1,1,3,3-tetramethylbutyl)-2-mercaptobenzimidazole, 6-cyclohexyl-2-mercaptobenzimidazole, 7-benzyl-2-mercaptobenzimidazole, 6-methoxy-2-mercaptobenzimidazole, 6-ethoxy-2-mercaptobenzimidazole, 7-ethoxy-2-mercaptobenzimidazole, 5-methoxy-2-mercaptobenzimidazole, 4-methylthio-2-mercaptobenzimidazole, 6-isopropoxy-2-mercaptobenzimidazole, 4-fluoro-2-mercaptobenzimidazole, 5-chloro-2-mercaptobenzimidazole, 5-chloro-2-mercaptobenzimidazole, 7-bromo-2-mercaptobenzimidazole, 6-chloro-2-mercaptobenzimidazole, 5-cyano-2-mercaptobenzimidazole, 4-phenyl-2-mercaptobenzimidazole, 6-nitro-2-mercaptobenzimidazole, 5-carboxy-2-mercaptobenzimidazole, 5-butoxycarbonyl-2-mercaptobenzimidazole, 7-hydroxy-2-mercaptobenzimidazole, 6-amino-2-mercaptobenzimidazole, 5-dimethylamino-2-mercaptobenzimidazole, 4-piperidino-2-mercaptobenzimidazole, 5-methylcarbamoyl-2-mercaptobenzimidazole, 5-diethylcarbamoyl-2-mercaptobenzimidazole, 5-chloro-6-n-butyl-2-mercaptobenzimidazole, 4-bromo-5-n-hexyl-2-mercaptobenzimidazole, 5-nitro-6-n-propyl-2-mercaptobenzimidazole, 5-bromo-6-n-propoxy-2-mercaptobenzimidazole, 4-nitro-7-butyl-2-mercaptobenzimidazole, 4,5,6-triethyl-2-mercaptobenzimidazole, 4,5,6,7-tetramethyl-2-mercaptobenzimidazole, 4-methoxy-6-hydroxy-2-mercaptobenzimidazole, 4,5-dimethyl-7-propoxy-2-mercaptobenzimidazole, 5-(or 6)-chloro-6-(or 5)-n-butyl-2-mercaptobenzimidazole, 4-(or 7)-bromo-5-(or 6)-n-hexyl-2-mercaptobenzimidazole, 5-(or 6)-nitro-6-(or 5)-n-propyl-2-mercaptobenzimidazole, 5-(or 6)-bromo-6-(or 5)-n-propoxy-2-mercaptobenzimidazole, 4-(or 7)-nitro-7-(or 4)-butyl-2-mercaptobenzimidazole, 4-(or 7)-, 5-(or 6)-, 6-(or 5)-triethyl-2-mercaptobenzimidazole, 4,5,6,7-tetramethyl-2-mercaptobenzimidazole, 4-(or 7)-methoxy-6-(or 5)-hydroxy-2-mercaptobenzimidazole, 4-(or 7)-, 5-(or 6)-dimethyl-7-(or 4)-propoxy-2-mercaptobenzimidazole, 5-methyl-2-mercaptobenzoxazole, 6-ethyl-2-mercaptobenzoxazole, 4-isopropyl-2-mercaptobenzoxazole, 7-t-butyl-2-mercaptobenzoxazole, 5-n-hexyl-2-mercaptobenzoxazole, 6-(1,1,3,3-tetramethylbutyl)-2-mercaptobenzoxazole, 6-cyclohexyl-2-mercaptobenzoxazole, 7-benzyl-2-mercaptobenzoxazole, 6-methoxy-2-mercaptobenzoxazole, 6-ethoxy-2-mercaptobenzoxazole, 7-ethoxy-2-mercaptobenzoxazole, 5-methoxy-2-mercaptobenzoxazole, 4-methylthio-2-mercaptobenzoxazole, 5-methylsulfonyl-2-mercaptobenzoxazole, 6-isopropoxy-2-mercaptobenzoxazole, 4-fluoro-2-mecaptobenzoxazole, 5-chloro-2-mercaptobenzoxazole, 7-bromo-2-mercaptobenzoxazole, 6-chloro-2-mercaptobenzoxazole, 5-cyano-2-mercaptobenzoxazole, 4-phenyl-2-mercaptobenzoxazole, 6-nitro-2-mercaptobenzoxazole, 5-carboxy-2-mercaptobenzoxazole, 7-hydroxy-2-mercaptobenzoxazole, 6-amino-2-mercaptobenzoxazole, 5-dimethylamino-2-mercaptobenzoxazole, 7-phenylamino- 2-mercaptobenzoxazole, 4-morpholino-2-mercaptobenzoxazole, 5-carbamoyl-2-mercaptobenzoxazole, 5-butylcarbamoyl-2-mercaptobenzoxazole, 6-dimethylcarbamoyl-2-mercaptobenzoxazole, 5-chloro-6-n-butyl-2-mercaptobenzoxazole, 4-bromo-5-n-hexyl-2-mercaptobenzoxazole, 5-nitro-6-n-propyl-2-mercaptobenzoxazole, 5-bromo-6-n-propoxy-2-mercaptobenzoxazole, 4-nitro-7-butyl-2-mercaptobenzoxazole, 4,5,6-triethyl-2-mercaptobenzoxazole, 4,5,6,7-tetramethyl-2-mercaptobenzoxazole, 4-methoxy-6-hydroxy-2-mercaptobenzoxazole and 4,5-dimethyl-7-propoxy-2-mercaptobenzoxazole and the salts of these compounds, for example the sodium, potassium, calcium, tetramethylammonium or trishydroxyethylammonium salts.

Examples of reactants of the formula V are bromomalonic acid, chlorosuccinic acid, bromosuccinic acid, p-toluenesulfonyloxysuccinic acid, 2-bromo-3,3-dimethylsuccinic acid, 2-chloromethylsuccinic acid, 2-bromomethylsuccinic acid, 2-bromoglutaric acid, 3-bromoglutaric acid, 2-chloro-3ethylsuccinic acid, 2-iodo-3,3-dimethylsuccinic acid, 2-bromo-2,3-dimethylsuccinic acid, 2-chloromethylglutaric acid, 2-(p-toluenesulfonyloxymethyl)-glutaric acid, 2-bromotricarballylic acid, 1-iodoethanetetracarboxylic acid, 1-bromocyclohexane-1,2-dicarboxylic acid, 2-iodo-2-butylsuccinic acid, 2-bromo-3-methoxymethylsuccinic acid, 2-chloro-3-hydroxymethylsuccinic acid, 2-bromo-3-phenylsuccinic acid, 2-iodo-3-benzylsuccinic acid, bromomaleic acid, 2-bromo-3-methylmaleic acid and 2-bromo-2,3-dimethylfumaric acid.

The compounds of the formula I in which X is —S— or —NH— and R⁴ is carboxyl can also be prepared in accordance with another process, which is the subject of a patent application by this Applicant Company. In this process, a compound of the formula IV in which X is —S— or —NH— and M is H, is reacted in a strongly acid medium with an α,β-unsaturated carboxylic acid of the formula VI

Examples of compounds of the formula VI are maleic acid, fumaric acid, mesaconic acid, citraconic acid, itaconic acid, aconitic acid, glutaconic acid or methyleneglutaric acid.

The compounds of the formula I can be used as corrosion inhibitors for metals, for example iron, steel, aluminium or copper, but especially for ferrous metals. This applies particularly to their use in aqueous systems in contact with metals, for example cooling water systems, air-conditioning plants, steam generating plants, sea water evaporation plants, heating and cooling water circulation systems and aqueous metal machining, antifreeze and hydraulic fluids.

The invention relates, therefore, to a process for protecting aqueous systems which are in contact with metals from corrosion, by adding a corrosion-inhibiting amount of a compound of the formula I, as defined initially, to the aqueous system.

In practice, the compound of the formula I is added to the aqueous system in an amount of 0.1 to 50,000 ppm, preferably 1 to 500 ppm. As well as the corrosion inhibitor, it is also possible to add other additives, such as are known for water treatment.

In the case of wholly aqueous systems, such as cooling water systems, air-conditioning plants, steam generating plants, sea water evaporation plants and heating and cooling water circulation systems, the additional corrosion inhibitors used can be, for example, water-soluble zinc salts, phosphates, polyphosphates, phosphonic acids and salts thereof, such as acetodiphosphonic acid, phosphonocarboxylic acids and salts thereof, for example nitrilotris(methylenephosphonic acid), the methylaminodimethylenephosphonocarboxylic acids of German Offenlegungsschrift 2,632,774, hydroxyphosphonoacetic acid, 2-phosphonobutane-1,2,4-tricarboxylic acid and the acids of British Patent 1,572,406, chromates, such as sodium chromate, nitrates, such as sodium nitrate, nitrites, such as NANO₂, molybdates, such as sodium molybdate, tungstates, silicates, benztriazoles and benztriazole derivatives, N-acylsarcosines, N-acylaminodiacetic acids, ethanolamines, fatty amines, polycarboxylic acids, for example polymaleic or polyacrylic acid and salts thereof, copolymers of maleic acid and acrylic acid and substitution derivatives of such (co)polymers.

To these mixtures can also be added dispersant assistants, for example polyacrylic acid and salts thereof, phosphinopolycarboxylic acids (as described in British Patent 1,458,235), hydrolysed polyacrylonitrile, polymethacrylic acid and salts thereof, polyacrylamide and copolymers thereof with acrylic or methacrylic acid, ligninsulfonic acid and salts thereof, taurine, naphthalenesulfonic acid/formaldehyde condensation products, starch and derivatives thereof and cellulose derivatives. Specific examples of these are 2-phosphonobutane-1,2,4-tricarboxylic acid, acetodiphosphonic acid, hydrolysed polymaleic anhydride and salts thereof, alkylphosphonic acids, hydroxyphosphonoacetic acid, 1- aminoalkyl-1,1-diphosphonic acids and salts thereof and alkali metal polyphosphonates.

It is also possible to add precipitants, such as alkali metal orthophosphates or alkali metal carbonates; oxygen acceptors, such as alkali metal sulfites and hydrazines; complexing agents, such as nitrilotriacetic acid and salts thereof; antifoaming agents, such as silicones, dicarboxylic acid fatty amides and ethylene oxide adducts of fatty alcohols or fatty amides; disinfectants, such as amines, quaternary ammonium salts, chlorophenols, sulfones, thiocyanates, carbamates, isothiazolones, brominated propionamides, triazines, phosphonium salts, chlorine and chlorine donors or organot in compounds.

The aqueous system can also be partly aqueous as in water-dilutable metal machining fluids, for example. Formulations of this type can, for example, be used for polishing, drilling, milling, cutting, sawing, drawing or flanging metals. On the basis of their formulation, the following types may be mentioned:

a) aqueous concentrates of one or more corrosion inhibitors and, if desired, of one or more anti-wear additives, which are used in a dilution of 1:50 to 1:100 as grinding fluids;

b) polyglycols containing biocides, corrosion inhibitors and anti-wear additives, which are used in a dilution of 1:20 to 1:40 as a cutting oil, and, in a dilution of 1:60 to 1:80, as a grinding oil;

c) semi-synthetic cutting oils similar to b), which also contain, in addition, 10–25% of an oil and also an appropriate amount of an emulsifier, in order to remain translucent when diluted with water;

d) an emulsifiable mineral oil concentrate, which can contain, for example, emulsifiers, corrosion inhibitors, high-pressure additives, biocides, antifoaming agents and other products. These are generally diluted with water in a ratio of 1:10 to 1:50, forming a white-opaque emulsion;

e) mineral oil concentrates similar to d), but which contain less oil and more emulsifier and which produce a translucent emulsion at a dilution of 1:50 to 1:100 and are used as cutting and grinding oils.

For such partly aqueous systems, such as are used as metal machining formulations, the corrosion inhibitor, according to the invention, of the formula I can be used on its own or as a mixture with other corrosion inhibitors or other additives. Examples of additional corrosion inhibitors are organic acids and esters and salts thereof, for example benzoic acid, p-tert.-butylbenzoic acid, sodium sebacate, triethanolamine laurate, isononanoic acid, the triethanolamine salt of p-toluenesulfonamidocaproic acid, triethanolamine salts of 5-ketocarboxylic acids of European Patent A-41,927 and sodium salts of N-lauroylsarcosine or phenoxyacetic acid; nitrogen-containing compounds, for example fatty acid alkanolamides, imidazolines, oxazolines, triazoles, in particular benztriazoles and Mannich bases derived therefrom, trialkanolamines, fatty amines, inorganic nitrates or nitrites or the carboxytriazines of European Patent A-46,139; phosphorus-containing compounds, such as amine phosphates and phosphonic acids and salts thereof, for example sodium dihydrogen phosphate or zinc phosphate; and sulfur-containing compounds, for example Na, Ca or Ba petroleumsulfonates or the sodium salt of mercaptobenzothiazole.

High-pressure additives can be used concomitantly as further additives. These are in most cases sulfur-containing, phosphorus-containing or halogen-containing compounds, for example sulfonated sperm oil, sulfonated fats, tritolyl phosphate, chloroparaffins or ethoxylated phosphoric esters.

An important factor for the use of the compounds of the formula I in aqueous systems is their good compatibility with hard water. This is based on the correspondingly high solubility of their alkaline earth metal salts.

The compounds of the formula I are also suitable for use as corrosion inhibitors in paints, for example in paints based on epoxide resins, polyurethanes, aminoplasts, acrylic resins, polyesters and alkyd resins. Further examples are paints based on polyvinyl butyral, phenolic resins, polyvinyl acetate, polyvinyl chloride, chlorinated rubber, styrene/butadiene copolymers, drying oils or cellulose esters. In this context the paints can be an aqueous system or an organic solution or can be solvent-free.

The examples which follow illustrate the present invention in greater detail. In these examples, parts and percentages are by weight, unless stated otherwise. The temperatures are quoted in °C.

EXAMPLE 1

A solution of 39.4 g of bromosuccinic acid in 200 ml of 10% aqueous $Na_2CO_3$ solution is added at 80°, with stirring and in the course of 30 minutes, to a solution of 41.5 g of 2-mercaptobenzthiazole in 200 ml of 10% $Na_2CO_3$ solution. The resulting solution is stirred for a further 2 hours at 80°. A dispersion is formed, which, after cooling to room temperature, is extracted with chloroform in order to remove unreacted mercaptobenzthiazole. The aqueous solution is then acidified with concentrated hydrochloric acid and extracted with diethyl ether. The ether solution is evaporated, and the solid residue is recrystallised from aqueous methanol. This gives benzthiazol-2-ylthiosuccinic acid, melting at 175°–178° (with decomposition). NMR spectrum ($\delta$, DMSO-$d_6$): 3.15 (d, 2H); 4.95 (t, 1H); 7.20–8.20 (c, 4H).

EXAMPLE 2

A solution of 19.7 g of bromosuccinic acid in 100 ml of 10% $Na_2CO_3$ solution is added, with stirring and in the course of 30 minutes, to a solution of 20.2 g of 5-chloro-2-mercaptobenzthiazole and 4 g of NaOH in 100 ml of water. The resulting suspension is heated at 90° for 2 hours and, after cooling, is filtered. The filtrate is acidified to pH 1 with concentrated hydrochloric acid, and the product thereby precipitated is filtered off and recrystallised from aqueous ethanol. This gives 5-chlorobenzthiazol-2-ylthiosuccinic acid, melting at 168°–173° (with decomposition).

Elementary analysis: calculated 41.58% C 2.53% H, 4.40% N $C_{11}H_8ClNO_4S_2$ found 41.78% C 2.63% H 5.68% N The following are prepared analogously: 6-nitrobenzthiazol-2-ylthiosuccinic acid, melting point 115°–118° (decomp.)

Analysis ($C_{11}H_8N_2O_6S_2$) calculated 40.20% C 2.46% H 8.54% N found 40.44% C 2.65% H 8.82% N 6-ethoxybenzthiazol-2-ylthiosuccinic acid, melting point 168°–170°.

Analysis ($C_{13}H_{13}NO_5S_2$) calculated 47.72% C 4.16% H 4.44% N found 47.40% C 4.15% H 4.15% N 6-aminobenzthiazol-2-ylthiosuccinic acid, melting point 115° (decomp.)

Analysis ($C_{11}H_{10}N_2O_4S_2$) calculated 44.28% C 3.38% H 9.39% N found 44.01% C 3.59% H 9.31% N.

EXAMPLE 3

4.06 g of 2-bromo-3,3-dimethylsuccinic anhydride and 2.12 g of $Na_2CO_3$ are stirred in 50 ml of water for one hour at 60°. The resulting solution is cooled to room temperature and added dropwise to a solution of 3.67 g of 2-mercaptobenzthiazole and 8 g of NaOH in 50 ml of water. When the addition is complete, the reaction mixture is heated at 80° for 2 hours. After cooling, concentrated hydrochloric acid is added until pH 1 is reached, and the precipitated product is filtered off. The product is purified by being dissolved in $Na_2CO_3$ solution and precipitated once again with HCl. This gives 2-(benzthiazol-2-ylthio)-3,3-dimethylsuccinic acid (=1-(benzthiazol-2-ylthio)-2-methylpropane-1,2-dicarboxylic acid), melting point 176°–178°.

EXAMPLE 4

A solution of 19.7 g of bromosuccinic acid in 100 ml of 10% $Na_2CO_3$ solution is added dropwise, at 80°, with stirring and in the course of 15 minutes, to a mixture of 13.68 g of 2-mercaptobenzoxazole and 100 ml of 10% $Na_2CO_3$ solution. When addition is complete, the mixture is heated at 85° for 6 hours. After cooling, the resulting suspension is extracted three times with ethyl acetate. The aqueous phase is acidified to pH 2 and is extracted with twice 100 parts by volume of ethyl acetate. The combined ethyl acetate solution is evaporated, and the residue is recrystallised from water. The crude product thus obtained is reprecipitated by dissolving in $NaHCO_3$ solution and precipitating with hydrochloric acid, and is recrystallised once more from water. This gives benzoxazol-2-ylthiosuccinic acid, melting at 154°–155°.

Analysis ($C_{11}H_{19}NO_5S$) calculated 49.45% C 3.40% H 5.24% N found 49.36% C 3.38% H 5.16% N.

EXAMPLE 5

16.8 g of finely powdered 2-mercaptobenzthiazole are suspended in 40 ml of 70% sulfuric acid, and 10.3 g of powdered maleic anhydride are added in the course of 1 hour at 48°–51°, with stirring. After a further hour at 50°, the reaction mixture is cooled to room temperature and diluted at 25°–35° by adding 250 ml of water dropwise. After 1 hour the precipitated product is filtered off and dissolved in dilute sodium hydroxide solution. The solution is filtered and acidified with hydrochloric acid. The precipitate is filtered off and dried in vacuo at 60°. This gives 24.7 g (87% of theory) of benzthiazol-2-ylthiosuccinic acid, melting with decomposition at 175°–1 76°.

Analysis ($C_{11}H_9NO_4S_2$) calculated 46.64% C 3.18% H 4.94% N 22.61% S found 46.6% C 3.4% H 5.0% N 22.5% S.

The same reaction is repeated using 12.1 g of maleic acid instead of the an hydride. 22.6 g (80% of theory) of benzthiazolylthiosuccinic acid are obtained.

The same reaction is carried out using 12.1 g of fumaric acid and the components are allowed to react for 12 hours at 40°. 21.1 g (75% of theory) of benzthiazolylthiosuccinic acid are obtained.

EXAMPLE 6

8.6 g of 6-chloro-2-mercapto-4-methylbenzthiazole are reacted as described in Example 5 with 4.4 g of maleic anhydride in 70% $H_2SO_4$ at 47°–50°. The crude product is purified by reprecipitation from $NaHCO_3$ solution. This gives 6-chloro-4-methylbenzthiazol-2-ylthiosuccinic acid, melting with decomposition at 168°–171°.

Analysis ($C_{12}H_{10}ClNO_4S_2$) calculated 43.44% C 3.04% H 4.22% N found 43.48% C 3.20% H 4.17% N.

5-Carboxybenzthiazol-2-ylthiosuccinic acid, melting with decomposition at 210°–215°, is obtained analogously from 20 g of 5-carboxy-2-mercaptobenzthiazole and 10.26 g of maleic anhydride.

Analysis ($C_{12}H_9NO_6S_2$) calculated 44.04% C 2.78% H 4.28% N found 43.9% C 2.78% H 4.39% N.

EXAMPLE 7

16.8 g of powdered 2-mercaptobenzthiazole are suspended in 50 ml of 70% sulfuric acid, and 13.7 g of itaconic acid are stirred into this suspension at 40°–44° in the course of 30 minutes. After a further 1.5 hours at 40°–44°, the reaction mixture is cooled to room temperature and diluted with water, keeping the temperature meanwhile below 35°. The precipitated 3-(benzthiazol-2-ylthio)-propane-1,2-dicarboxylic acid is filtered off, washed with cold water and dried at 60° in vacuo. Yield 27.5 g (92% of theory), melting point 160°14 166°.

Analysis ($C_{12}H_{11}NO_4S_2$) calculated 48.48% C 3.73% H 4.71% N 21.57%S found 48.2% C 3.7% H 4.6% N 21.3% S.

3-(6-Nitrobenzthiazol-2-ylthio)-propane-1,2-dicarboxylic acid, melting with decomposition at 190°–198°, is obtained analogously from 84.2 g of 6-nitro-2-mercaptobenzthiazole and 52.4 g of itaconic acid.

EXAMPLE 8

20.9 g of 2-methyleneglutaric acid are dissolved at 50°, with stirring, in 150 ml of 75% $H_2SO_4$, and 24.2 g of 2-mercaptobenzthiazole are added slowly. The reaction is exothermic and the temperature rises to 60°. The reaction mixture is then stirred for 2 hours at 55°. The resulting brown solution is poured into 500 ml of water and stirred for 1 hour. 600 ml of water are then added, and the white precipitate is filtered off. Recrystallisation from aqueous methanol gives 4-(benzthiazol-2-ylthio)-butane-1,3-dicarboxylic acid, melting at 152°–154°.

Analysis ($C_{13}H_{13}NO_4S_2$) calculated 50.14% C 4.21% H 4.50% N found 50.39% C 4.35% H 4.36% N.

EXAMPLE 9

16.8 g of 2-mercaptobenzthiazole are suspended in 50 ml of 70% $H_2SO_4$, and 13.7 g of glutaconic acid are added at 45°–50°, with stirring and in the course of 30 minutes. The reaction mixture is stirred at 45°–50° for a further 1.5 hours, and the product is isolated as described in Example 5. This gives 26 g (88% of theory) of 3-(benzthiazol-2-ylthio)-glutaric acid, melting at 153°–154°.

Analysis ($C_{12}H_{11}NO_4S_2$) calculated 48.48% C 3.71% H 4.71%, N 21.57% S found 48.5% C 3.8% H 4.8 % N 21.2% S.

EXAMPLE 10

4.45 g of 2-mercaptobenzthiazole and 5 g of but-3-ene-1,2,3-tricarboxylic acid are ground with one another in a mortar. The powdered mixture is introduced in portions and with stirring into 60 ml of 70% $H_2SO_4$ at 48°–50°, in the course of one hour. After a further 3 hours at 48°–50°, the reaction mixture is cooled to room temperature and diluted with 250 ml of water at 25°–30°, with stirring. The aqueous solution is decanted from a little tacky deposit and is diluted with a further 200 ml of water. After being stirred for 1 hour the precipitate is filtered off and dried. The 4-(benzthiazol-2-ylthio)-butane-1,2,3-tricarboxylic acid obtained melts at 188°-190° after recrystallisation from methanol/water.

Analysis $C_{14}H_{13}NO_6S_2$ calculated 47.32% C 3.69% H 3.74% N found 47.40% C 3.86% H 3.89% N.

EXAMPLE 11

47.4 g of 2-mercaptobenzimidazole are reacted in the same manner as in Example 10 with 40.7 g of itaconic acid in 150 ml of 70% $H_2SO_4$ at 40°-43°. After dilution with water, sodium hydroxide solution is added until pH 4 is reached, the product being precipitated as the dihydrate. Anhydrous 3-(benzimidazol-2-ylthio)-propane-1,2-dicarboxylic acid, melting at 165°-168°, is obtained from the dihydrate by recrystallisation.

EXAMPLE 12

8.56 g of benzthiazol-2-ylthiosuccinic acid are dissolved, with stirring, in 60 ml of 1 N NaOH solution. A solution of 3.33 g of $CaCl_2$ in a little water is added dropwise. The resulting precipitate of calcium benzthiazol-2-ylthiosuccinate is filtered off, washed with a little cold water and dried in vacuo at 100°.

Analysis calculated 41.12% C 2.20% H 4.36% N 12.47% ($C_{11}H_7CaNO_4S_2$) found 40.69% C 2.36% H 4.23% N 12.40%

The corresponding zinc salt, which is obtained as the monohydrate, is precipitated analogously from 8.56 g of benzthiazol-2-ylsuccinic acid in 100 ml of methanol and 6.58 g of zinc acetate in 70 ml of methanol.

Analysis calculated 36.23% C 2.49% H 3.84% N 17.56% S ($C_{11}H_7NO_4S_2Zn.H_2O$) found 36.54% C 2.46% H 3.79% N 17.68% S

EXAMPLE 13

A solution of 8.26 g of mercaptosuccinic acid in 50 ml of 10% $Na_2CO_3$ solution is added dropwise, with stirring, to a solution of 8.48 g of 2-chlorobenzthiazole in 50 ml of dioxane. When the addition is complete, the reaction mixture is stirred for 4 hours at 85° and is then cooled.

A solution of 4 g of NaOH in 20 ml of water is then added, and the reaction mixture is stirred for a further 5 hours at 85°. After cooling, the solution is acidified with concentrated hydrochloric acid and extracted with three times 30 ml of ethyl acetate. The combined extracts are dried over $Na_2SO_4$ and evaporated. The solid residue is washed with 1:1 hexane/diethyl ether and is taken up in $NaHCO_3$ solution. The solution is freed from undissolved matter by filtration, washed with chloroform and acidified with hydrochloric acid. The product thus precipitated is extracted with ethyl acetate. The product obtained by evaporating the ethyl acetate solution is recrystallised from water to give benzthiazol-2-ylthiosuccinic acid which is identical with the compound prepared in accordance with Example 1.

EXAMPLE 14

A solution of 15.0 g of 6-nitrobenzthiazol-2-ylthiosuccinic acid (prepared in accordance with Example 2) in 70 ml of aqueous ammonia (d 0.95) is saturated with hydrogen sulfide while being cooled at 25°-30° by means of an ice bath. The deep red solution is heated to 90° in the course of one hour and is kept at this temperature for 1 hour. The resulting suspension is cooled and its pH is adjusted to 5 with acetic acid, the temperature being kept meanwhile below 35° by cooling.

The precipitate is filtered off rapidly and washed with a little water. The filtrate is stirred at room temperature for several hours, in the course of which the product slowly crystallises out. The crystals are filtered off and recrystallised from methanol. This gives 6-aminobenzthiazol-2-ylthiosuccinic acid, melting point 117°, which is identical with the compound obtained in accordance with Example 2.

3-(6-Aminobenzthiazol-2-ylthio)-propane-1,2-dicarboxylic acid, melting with decomposition at 182°-185°, is obtained analogously by reducing 3-(6-nitrobenzthiazol-2-ylthio)-propane-1,2-dicarboxylic acid (obtained in accordance with Example 7).

Analysis ($C_{12}H_{12}N_2O_4S_2$) calculated 46.15% C 3.88% H 8.97% N found 46.38% C 4.23% H 9.01% N.

EXAMPLE 15

The corrosion-inhibiting action of the compounds according to the invention is demonstrated below by means of a test with aerated water. The water used for this test is of a standardised corrosivity, prepared by dissolving 20 g of $CaSO_4.2H_2O$, 15 g of $MgSO_4.7H_2O$, 4.6 g of $NaHCO_3$ and 7.7 g of $CaCl_2.6H_2O$ in 166 l (45 gallons) of distilled water. Steel sheets (composed of soft mild steel) measuring $5 \times 2.5$ cm are scoured with pumice powder, immersed for one minute in hydrochloric acid, rinsed, dried and weighed. 10 mg of the corrosion inhibitor are dissolved in each case in 100 ml of the standard water, which corresponds to a concentration of 100 ppm. The sheet is hung in the solution, and the vessel is controlled thermostatically at 40°. Air is passed through the solution at a rate of 500 ml/minute. The water thus evaporated is replaced continuously by distilled water, so that the liquid level in the vessel remains constant.

A sheet is taken out after 48 hours, scoured with pumice, immersed for one minute in hydrochloric acid which has been inhibited by adding 1% of hexamethylenetetramine, and is then rinsed, dried and weighed. A blank sample with no corrosion inhibitor is also run for each test. The corrosion rate (CR) is calculated from the loss in weight in mg per $dm^2$ of metal surface per day of the duration of the test. The percentage inhibition of corrosion is calculated from the difference between the blank sample and the sample, in accordance with the formula $$\text{Percentage inhibition of corrosion} = \frac{CR \text{ of blank sample} - CR \text{ of sample}}{CR \text{ of blank sample}} \times 100$$

The results are listed in Table 1.

TABLE 1

| Corrosion inhibitor (100 ppm) | Percentage of inhibition of corrosion |
|---|---|
| 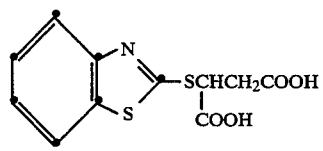 | 100 |

TABLE 1-continued

| Corrosion inhibitor (100 ppm) | Percentage of inhibition of corrosion |
|---|---|
| 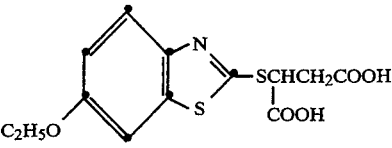 | 99 |
| 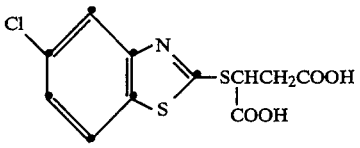 | 100 |
| 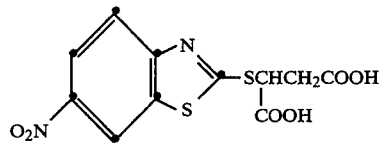 | 89 |
| 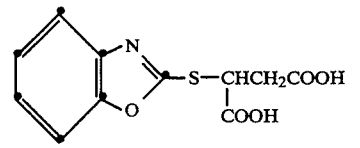 | 70 |

EXAMPLE 16

The effectiveness of the corrosion inhibitors of the formula I in metal machining fluids can be demonstrated by Method IP 287 of the Institute of Petroleum. For this purpose a 1% solution of the corrosion inhibitor in water containing 68 mg of $CaCl_2.6H_2O$ and 132 mg of $MgSO_4.7H_2O$ per liter is brought to a pH of 8.5 by adding triethanolamine.

The base of a Petri dish of diameter 90 mm is covered with filter paper, and the latter is covered, for an area of 35×35 ram, with a thin layer of cast iron turnings (prepared by Method IP 287). An amount of 2 ml of the inhibitor solution is pipetted onto the turnings, the lid is placed on the Petri dish, and the latter is allowed to stand for 2 hours at room temperature. The filter paper is then taken away, the turnings are rinsed with water, and the rust pattern on the filter paper is assessed. The following assessment scale is used in Table 2:

0 no rust specks
1 1–3 specks, less than 1 mm in diameter
2 up to 1% of the area covered with specks
3 up to 5% of the area covered with specks
4 >5% of the area covered with specks The test is also carried out with a 0.5% inhibitor solution. The results are listed in Table 2.

TABLE 2

| Corrosion inhibitors | Rust pattern at a concentration of | |
|---|---|---|
| | 1% | 0.5% |
| 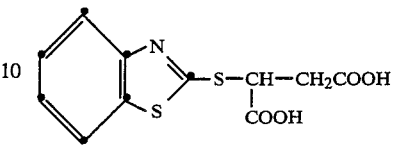 | 0 | 3 |
| 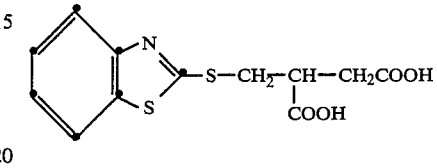 | 0 | 3 |
| 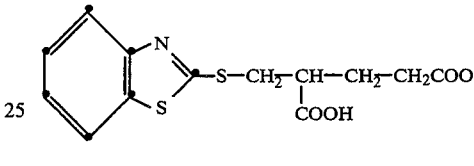 | 0 | 0 |
| 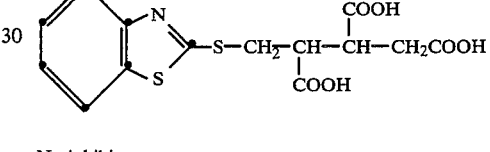 | 0 | 0 |
| No inhibitor | 4 | 4 |

A visual assessment of the 1% solutions of the compounds listed in the table shows that no precipitation or cloudiness can be discerned within a day. This shows that these compounds are not sensitive to water hardness.

EXAMPLE 17

A primer composed of an aromatic epoxide resin, red iron oxide, talc and a polyaminoamide curing agent is sprayed on to sand-blasted steel sheets and cured for 1 week at room temperature. A white top lacquer composed of a two-component polyurethane is applied to the sheets and is also allowed to cure for one week. The primer contains the corrosion inhibitor indicated in Table 3. An X-shaped cut extending into the metal is cut in the lacquered sample by means of a type 463 Sikkens knife. The sheets are then subjected to a salt spray tests as specified in ASTM B 117. Lasting 1,000 hours. The results are listed in Table 3.

TABLE 3

| Corrosion inhibitor | Bubble formation | Sub-surface corrosion |
|---|---|---|
| none | severe | severe |
| 3% of compound 1 | little | slight |
| 6% of compound 1 | none | none |

Compound 1 = benzthiazol-2-ylthiosuccinic acid

What is claimed is:
1. An organic amine addition salt of a compound of formula I

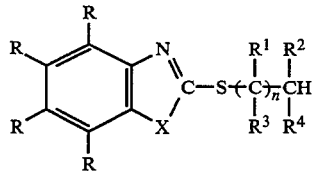

in which each of R independently of the others is H, $C_1-C_{12}$-alkyl, $C_1-C_{12}$alkoxy, $C_1-C_4$-halogenoalkyl, $C_1-C_{12}$-alkylthio, $C_1-C_{12}$-alkylsulfonyl, phenyl, $C_7-C_{16}$-alkylphenyl, $C_7-C_{16}$-phenylalkyl, $C_5-C_8$-cycloalkyl, halogen, $-NO_2$, $-CN$, $-COOH$, $-COO(C_1-C_4$-alkyl), $-OH$ or $-NH_2$, X is $-S-$, n is zero or 1, and when n is 1, $R^1$, $R^2$, $R^3$ and $R^4$ independently of one another are H, $C_1-C_{18}$-alkyl, $C_1-C_4$-hydroxyalkyl, $C_2-C_{12}$-mono-, di- or tri-carboxyalkyl, $C_1-C_4$-halogenoalkyl, $C_2-C_{10}$ -alkoxyalkyl, $-COOH$ or aryl or aralkyl having 6 to 10 C atoms, or said aryl or said arallkyl substituted with $C_1-C_4$-alkyl, $C_1-C_4$-alkoxy, $-NO_2$, $-COOH$, $-OH$ or halogen, or $R^1$ and $R^2$ together are linear or branched $C_3-C_8$-alkylene which is unsubstituted or substituted with 1 or 2 carboxyl groups, or $R^1$ and $R^2$ together are a direct bond, and when n is zero, $R^2$ and $R^4$ are carboxyl, subject to the proviso that the group

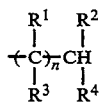

contains at least two and not more than four carboxyl groups.

2. An organic amine salt of a compound of formula I according to claim 1, in which one R is hydrogen, $C_1-C_4$-alkyl, $C_1-C_4$-alkoxy or $-NH_2$ and the other three Rs are hydrogen.

3. An organic amine salt of a compound of formula I according to claim 1, in which all four Rs are hydrogen.

4. An organic amine salt of a compound of formula I according to claim 1, in which two of the groups $R^1$, $R^2$, $R^3$ and $R^4$ are carboxyl or carboxyalkyl groups.

5. An organic amine salt of a compound of formula I according to claim 1, in which n is 1 and $R^1$, $R^2$, $R^3$ and $R^4$ independently of one another are H, $C_1-C_{12}$-alkyl, $C_1-C_4$-hydroxyalky, $C_2-C_6$-carboxyalkyl, $C_2-C_{10}$-alkoxyalkyl, carboxyl, phenyl or benzyl, or $R^1$ and $R^2$ together are trimethylene or tetramethylene.

6. An organic amine salt of a compound of formula I according to claim 1, in which n is 1 and $R^1$, $R^2$, $R^3$ and $R^4$ independently of one another are H, $C_1-C_4$-alkyl, carboxyl or $C_2-C_6$-carboxyalkyl.

7. An organic amine salt of a compound of formula I according to claim 1 which is

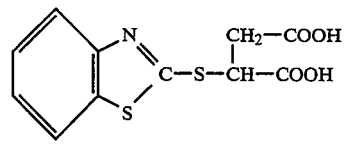

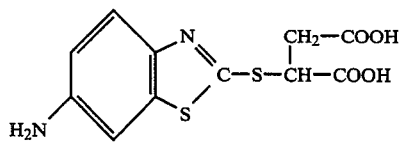

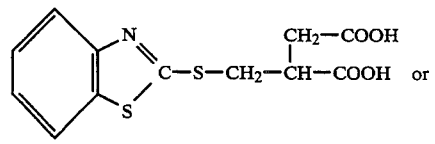

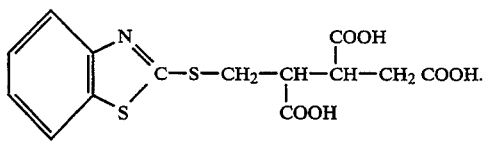

8. An organic amine salt according to claim 1 wherein the organic amine is selected from the group consisting of methylmine, ethanolmine, diethylamine, dibutylamine, diethanolarnine, cyclohexylamine, trimethylamine, triisopropylarnine, trioctylamine and triethanolamine.

* * * * *